(12) United States Patent
Faergemann et al.

(10) Patent No.: US 7,973,080 B2
(45) Date of Patent: Jul. 5, 2011

(54) METHOD FOR INHIBITING THE GROWTH OF ANTIBIOTIC RESISTANT OF BACTERIA BY USING PENTANE-1,5-DIOL

(75) Inventors: Jan Faergemann, Göteborg (SE); Thomas Hedner, Gällstad (SE)

(73) Assignee: Ambria Dermatology AB, Helsingborg (SE)

( * ) Notice: Subject to any disclaimer, the term of this patent is extended or adjusted under 35 U.S.C. 154(b) by 1286 days.

(21) Appl. No.: 10/562,608

(22) PCT Filed: Jun. 23, 2004

(86) PCT No.: PCT/SE2004/001001
§ 371 (c)(1),
(2), (4) Date: Apr. 28, 2006

(87) PCT Pub. No.: WO2004/112765
PCT Pub. Date: Dec. 29, 2004

(65) Prior Publication Data
US 2007/0020322 A1  Jan. 25, 2007

(30) Foreign Application Priority Data

Jun. 26, 2003 (SE) .................................... 0301862

(51) Int. Cl.
*A01N 33/02* (2006.01)
*A01N 25/34* (2006.01)
*A61K 31/13* (2006.01)
*B32B 5/02* (2006.01)
*B32B 27/04* (2006.01)
*B32B 27/12* (2006.01)

(52) U.S. Cl. ................... 514/638; 442/123; 424/448
(58) Field of Classification Search ........... 514/638; 442/123; 424/448
See application file for complete search history.

(56) References Cited

U.S. PATENT DOCUMENTS

| | | | |
|---|---|---|---|
| 5,369,129 A * | 11/1994 | Swanbeck et al. | 514/738 |
| 5,370,876 A * | 12/1994 | Noll et al. | 424/407 |
| 5,411,597 A * | 5/1995 | Tsao et al. | 134/26 |
| 5,550,145 A | 8/1996 | Olund et al. | |
| 5,879,690 A | 3/1999 | Perricone | |
| 6,348,203 B1 * | 2/2002 | Goodman et al. | 424/401 |
| 2002/0192273 A1 * | 12/2002 | Buseman et al. | 424/449 |

FOREIGN PATENT DOCUMENTS

| | | |
|---|---|---|
| EP | 1166762 B1 | 10/2002 |
| WO | WO 90/15597 A1 | 12/1990 |
| WO | WO 93/20812 | 10/1993 |
| WO | WO 01/07003 A1 | 2/2001 |

OTHER PUBLICATIONS

Antibiotic Resistance' (http://en.wikipedia.org/wiki/ Antibiotic_resistance), 2010.*
Todar (Todar's Online Textbook of Bacteriology, Chapter, Bacterial Resistance to Antibiotics, p. 1-4) 2008.*
Moinuddin (http://www.apic.org/AM/AMTemplate.cfm?Section=Brochures&Template=/CM/ContentDisplay.cfm &ContentFileID=2573, 2005).*
Huff (Naturalnews.com, Mar. 6, 2010).*
Baker (Naturalnews.com, Jul. 18, 2009).*
(Bamberger, Am Fam Physician, 72, Dec. 2005).*
1,5 pentane diol, CAS Registry, 2010, p. 1.*
'Beta-lactamases' (http://en.wikipedia.org/wiki/Beta-lactamase), p. 1-15, 2010.*
Coagulation negative Staph—'http://www.dhh.louisiana.gov/offices/miscdocs/docs-249/vet/ulti%20drug%20resistance/09/StaphCN08.pdf'—p. 1, 2008.*
Kataoka et al. (Intl J of Antimicrobial Agents 22, 2003, 601-606).*
Sedghi Zadeb et al., "Inhibitori della crescita microbica", Cosmetic technology, vol. 4, No. 3, pp. 43-48 (2001).
International Search Report dated Nov. 2, 2004.
Sakagami Yoshikazu,; "Beneficial Effect of Disinfectant and Proper Use Thereof"; Medical Technology, 1991, vol. 19, No. 11, pp. 978-984 (Partial English translation).

* cited by examiner

*Primary Examiner* — Sreeni Padmanabhan
*Assistant Examiner* — Uma Ramachandran
(74) *Attorney, Agent, or Firm* — Dickstein Shapiro LLP

(57) ABSTRACT

A method for inhibiting the growth of multiple-resistant bacteria comprises the topical administration of a pharmaceutical composition comprising 15% by weight or more of pentane-1,5-diol and a pharmaceutical acceptable carrier. Also disclosed is a method of preparing a corresponding medicament. A method of disinfecting a surface contaminated with multiple-resistant bacteria comprises providing a disinfecting composition comprising 15% or more by weight of pentane-1,5-diol and an aqueous carrier, applying the composition to the surface; optionally, keeping it in contact with the surface for a period of time from 5 min to 24 hrs at ambient temperature, and rinsing the surface with water or an aqueous detergent composition. Also disclosed is the use of a corresponding bacteriostatic composition.

16 Claims, No Drawings

METHOD FOR INHIBITING THE GROWTH OF ANTIBIOTIC RESISTANT OF BACTERIA BY USING PENTANE-1,5-DIOL

FIELD OF THE INVENTION

The present invention relates to a method for inhibiting the growth of multiple-resistant bacteria and a method for the manufacture of a corresponding composition, to such a composition and to uses of the composition.

BACKGROUND OF THE INVENTION

Infection caused by antibiotic-resistant strains of bacteria, often termed "multiple-resistant", are a major problem in health care. By "multiple-resistant" understood the resistance against at least one antibiotic known to be effective against a corresponding non-resistant strain. In the context of this specification an antibiotic is an agent which can be administered topically to a person in form of a pharmaceutical, and which composition specifically interacts with the metabolism of the bacterium or bacteria against which it is used. The term antibiotic thus excludes mere disinfectants which exhibit a non-specific antimicrobial action which are harmful also to the skin and for which the skin can be exposed for a short time at best or not at all, such as chlorhexidine and aqueous hypochlorite, respectively.

Multiple-resistant bacteria strains are known to emerge due to the often excessive use of antibiotics. In order to keep the propagation of multiple-resistant bacteria at bay, strict infection control measures are called for as well as a more restrictive use of antibiotics.

The most important nosocomial resistance problems are caused by methicillin-resistant *Staphylococcus aureus*, vancomycin-resistant enterococci, and enterobacteriaceae with plasmid-encoded extended-spectrum β-lactamases.

OBJECTS OF THE INVENTION

It is an object of the invention to provide a method for inhibiting the growth of multiple-resistant bacteria.

It is a further object of the invention to provide such a method in which there is no risk of further selection of multiple-resistant bacterial strains.

It is an additional object of the invention to provide a method for the manufacture of a composition for inhibiting the growth of multiple-resistant bacteria.

Further objects of the invention will become apparent from the following summary of the invention, the description of preferred embodiments thereof, and the appended claims.

SUMMARY OF THE INVENTION

The present invention is based on the insight that pentane-1,5-diol is effective against multiple-resistant bacteria. The inventors have found that compositions comprising 15% by weight of more of pentane-1,5-diol and a suitable carrier that lacks bacteriostatic effect or the bacteriostatic effect of which is less than 5% on a weight basis of the bacteriostatic effect of pentane-1,5-diol in respect of a particular microorganism provide efficient bacteriostasis against multiple-resistant bacteria. This is entirely unexpected even in view of the known moderate antibacterial effect of pentane-1,5-diol and similar diols. In addition, there is reason to believe that the bacteriostatic effect of the invention is shared by other low-molecular weight aliphatic diols, such as propane-1,2-diol, propane-1,3-diol, butane-1,2-diol, butane-1,3-diol, butane-1,4-diol, butane-2,3-diol, 2-methylpropane-1,2-diol, 2-methylpropane-1,3-diol, 2-hydroxymethyl-1-propanol, pentane-1,2-diol, pentane-2,3-diol, 2-hydroxymethyl-1-butanol, 2-methylbutane-1,2-diol, 3-methylbutane-1,2-diol, 2-methylbutane-1,3-diol, 3-methylbutane-1,3-diol, 2-methylpentane-1,4-diol, hexane-1,2-diol, hexane-1,6-diol, 2-methylpentane-1,5-diol, 3-methylpentane-1,5-diol.

Due to the low acute and long-term toxicity of pentane-1,5-diol the bacteriostatic composition of the invention may be used as a pharmaceutical for topical administration but also as a disinfectant which, in contrast to other efficient disinfectants, poses no health risk to persons using it. An additional advantage of the composition of the invention is that it does not give rise to resistant strains of bacteria.

The composition of the invention may take the form of a liquid, semi-liquid or solid disinfectant preparation, a bacteriostatic solution, lotion, cream, soap, shampoo, ointment, paste, wet towel, hygiene dish, patch, diaper or similar personal hygiene protection device.

In a preferred embodiment the composition of the invention is combined with antibiotic, antiviral agent, antiseptic, agent for treatment of acne and with other agents used in the treatment of infectious diseases of the skin and the mucous membranes.

In another preferred embodiment the composition of the invention comprises an anionic emulsifier, such as Cetylanum.

If intended for application to the skin or mucous membranes, the composition of the invention preferably comprises one or several of tonicity adjustment agent such as sodium chloride, moisturizing agent such as carbamide and lactic acid, UV-absorbing agent, colorant such as calcium carbonate and zinc oxide, and fragrant such as an aetheric oil. The composition of the invention may also comprise a cationic, neutral, or anionic detergent, in particular a salt of a fatty acid.

More particularly, according to the present invention is disclosed a method for inhibiting the growth of multiple-resistant bacteria by topical administration of a pharmaceutical composition comprising more 15% by weight or more of pentane-1,5-diol and a pharmaceutical acceptable carrier such as an aqueous carrier, in particular water or saline. The pharmaceutical composition preferably consists of pentane-1,5-diol and pharmaceutical acceptable carrier. Topical administration by a patch of a woven or non-woven material or a combination of these materials provided with the composition is particularly preferred.

According to the invention is also disclosed a method of manufacture of a medicament for topical administration for inhibiting the growth of multiple-resistant bacteria, said method comprising the incorporation of 15% by weight or more of 1,5-pentanediol in a pharmaceutically acceptable carrier. The pharmaceutically acceptable carrier preferably has no bacteriostatic effect of its own or a bacteriostatic effect which is less than 5% on a weight basis of the bacteriostatic effect of pentane-1,5-diol in respect of a particular microorganism. It is also preferred for the carrier to comprise a patch of a woven or non-woven material or a combination of these materials. The carrier is preferably an aqueous carrier.

According to an advantageous aspect of the invention is disclosed a method for inhibiting the growth of multiple-resistant bacteria by application of a bacteriostatic composition comprising 15% by weight or more of pentane-1,5-diol and a suitable carrier to a non-porous surface (metal, wood, lacquer, plastic . . . ) contaminated with said bacteria. Preferably this bacteriostatic composition essentially consists of pentane-1,5-diol and a carrier which is essentially free from other bacteriostatic agents. It is preferred for the carrier to be an aqueous carrier which advantageously may comprise a thickening agent. Preferred thickening agents are agents selected from cellulose derivatives, in particular methyl cellulose, hydroxymethyl cellulose, hydroxymethyl-propyl cellulose. According to a further advantageous aspect of the invention the carrier comprises a salt of a fatty acid. According to a still further advantageous aspect of the invention the bacteriostatic composition is comprised by a patch of a woven or non-woven material or a combination thereof.

According to the invention is also disclosed the use of a composition comprising 15% or more by weight of pentane-1,5-diol and a suitable carrier for inhibiting the growth of multiple-resistant bacteria. Preferably the carrier is an aqueous carrier, optionally comprising a thickening agent selected from cellulose derivatives, in particular methyl cellulose, hydroxymethyl cellulose, hydroxymethyl-propyl cellulose. The carrier may advantageously include a patch of a woven or non-woven material or a combination thereof.

According to the invention is furthermore disclosed a method of disinfecting a surface contaminated with multiple resistant bacteria, comprising:
  providing a disinfecting composition comprising 15% or more by weight of pentane-1,5-diol and a suitable carrier;
  applying said composition to said surface;
  optionally, keeping said composition in contact with said surface for a period of time from 5 min to 24 hours at ambient temperature,
  rinsing said surface with water or an aqueous detergent composition.

The present invention will now be explained by reference to a number of preferred embodiments, which are only given to illustrate but not limit the invention.

DESCRIPTION OF PREFERRED EMBODIMENTS

Example 1

Determination of inhibitory activity of pentane-1,5-diol against bacteria. The minimum inhibitory concentration (MIC) of pentane-1,5-diol for a number of bacteria was assessed by a standard blood agar dilution technique (24 hrs, 37° C.). Agar samples with pentane-1,5-diol concentrations increasing in steps of 2.5% by weight were prepared by mixing the components at a temperature above the solidifying temperature of the agar prior to solidification. The following bacteria were investigated: methicillin-resistant *Staphylococcus aureus* (MSRA), fucidic acid-resistant *S. aureus*, non-resistant *S. pyogenes*, coagulation-negative staphylococci (for resistance, see Table 1 below) vancomycin-resistant enterococci (*Enterococcus* CCUG van A and van B), non-resistant *Escherichia coli*, *Acinetobacter* resistant against cefadroxil, nitrofurantin, mecillinam, *Serratia maltophilia* resistant against most types of antibiotics, *Enterobacter* (for resistance, see Table 1 below; additionally resistant against cefadroxil and nitrofurantin), non-resistant α-streptococci, non-resistant *Streptococcus* Group G, *Pseudomonas aeruginosa* (for resistance, see Table 2 below). Inocula of $10^3$ and $10^5$ bacteria were used. No major difference between the inocula was seen. This indicates that the inhibitory effect of pentant-1,5-diol is essentially independent of the inoculum size which contrasts to the behavior of the majority of conventional antibiotics. The results are given in Tab. 1 and 2; resistance is indicated against selected antibiotics only.

TABLE 1

Inhibitory effect of pentane-1,5-diol on various bacteria, including multiple-resistant (MR) bacteria; two inoculate sizes.

| Bacterial strain | MIC (% by weight of pentane-1,5-diol) | | MR against | | | | |
|---|---|---|---|---|---|---|---|
| | Inoculate Size $10^3$ | Inoculate Size $10^5$ | fuc | met | van | cip | tri |
| *S. aureus* 916 × 8143 | 12.5 | 12.5 | − | | | | |
| *S. aureus* 916 × 8137 | 12.5 | 10.0 | − | | | | |
| *S. aureus* 916 × 8163 | 12.5 | 17.5 | + | | | | |
| *S. aureus* 916 × 8150 | 12.5 | 15.0 | − | | | | |
| *S. aureus* 916 × 8184 | 10.0 | 12.5 | + | | | | |
| *S. aureus* 916 × 8155 | 10.0 | 12.5 | − | | | | |
| *S. aureus* 916 × 8183 | 12.5 | 17.5 | − | | | | |
| *S. aureus* 916 × 8180 | 12.5 | 15.0 | − | | | | |
| *S. aureus* 916 × 8181 | 12.5 | 15.0 | − | | | | |
| *S. aureus* 916 × 8191 | 12.5 | 15.0 | − | | | | |
| *S. aureus* 916 × 8158 | 12.5 | 15.0 | − | | | | |
| Coag.neg.staph. 900 × 5539 | 7.5 | 10.0 | − | | | | |
| Coag.neg.staph. 900 × 5515 | 12.5 | 15.0 | + | | | | |
| Coag.neg.staph. 900 × 5538 | 5.0 | 12.5 | − | | | | |
| Coag.neg.staph. 900 × 5525 | ND | 7.5 | − | | | | |
| Coag.neg.staph. 900 × 5516 | 7.5 | 12.5 | − | | | | |
| Coag.neg.staph. 904 × 2816 | 10.0 | 17.5 | + | | | | |
| Coag.neg.staph. 902 × 14176 large | 7.5 | 20.0 | − | | | | |
| Coag.neg.staph. 902 × 14176 small | 7.5 | 10.0 | + | | | | |
| Coag.neg.staph. 916 × 8132 | 7.5 | 12.5 | − | | | | |
| Coag.neg.staph. 916 × 8188 | 15.0 | 17.5 | − | | | | |
| MRSA CCUG 47019 | 10.0 | 17.5 | + | + | | | |
| MRSA CCUG 46870 | 10.0 | 17.5 | + | + | | | |
| MRSA CCUG 46740 | 12.5 | 17.5 | + | + | | | |
| MRSA CCUG 46618 | 12.5 | 15.0 | + | + | | | |
| MRSA CCUG 46463 | 10.0 | 15.0 | + | + | | | |
| MRSA CCUG 45008 | 12.5 | 15.0 | + | + | | | |
| MRSA CCUG 45007 | 10.0 | 12.5 | + | + | | | |
| MRSA PB/SS | 12.5 | 15.0 | + | + | | | |
| MRSA Cypem | 7.5 | 10.0 | + | + | | | |
| MRSA CCUG 41787 | 12.5 | 17.5 | + | + | | | |
| *Enterococcus* 921 × 57057 | 7.5 | 10.9 | + | − | | | − |
| *Enterococcus* 921 × 57022 | 5.0 | 7.5 | + | − | | + | + |
| *Enterococcus* 921 × 57002 | 7.5 | 10.0 | + | − | | | − |
| *Enterococcus* 921 × 57093 | 7.5 | 10.0 | + | − | | | + |
| *Enterococcus* 921 × 57158 | 7.5 | 7.5 | + | − | | | + |
| *Enterococcus* CCUG 39128 vanA | 5.0 | 10.0 | + | | + | | |
| *Enterococcus* CCUG 43324 vanA | 7.5 | 10.0 | + | | + | | |
| *Enterococcus* CCUG 37832 vanA | 5.0 | 7.5 | + | | + | | |
| *Enterococcus* CCUG 37593 vanB | 5.0 | 7.5 | + | | + | | |
| *E. coli* 921 × 57418 | 5.0 | 10.0 | | | | | |
| *E. coli* 921 × 57397 | 5.0 | 10.0 | | | | | |
| *E. coli* 921 × 57389 | 5.0 | 10.0 | | | | | |
| *E. coli* 921 × 57388 | 5.0 | 10.0 | | | | | |
| *E. coli* 921 × 57387 | 5.0 | 10.0 | | | | | + |
| *Enterobacter* 921 × 57574 | 5.0 | 10.0 | | | | | − |
| *Enterobacter* 921 × 57514 | 5.0 | 10.0 | | | | | − |
| *Enterobacter* 921 × 57416 | 5.0 | 10.0 | | | | | − |
| *Enterobacter* 921 × 57119 | 5.0 | 10.0 | | | | | − |
| *Enterobacter* 921 × 57100 | 5.0 | 10.0 | | | | | − |
| *Enterobacter* 921 × 57097 | 5.0 | 10.0 | | | | | − |
| *P. aeruginosa* CCUG 17619 | 5.0 | 5.0 | | | | | |
| *P. aeruginosa* 921 × 57855 | ND | 10.0 | | | | + | − | fuc = fucidin;
met = methicillin;
van = vancomycin;
cip = ciprofloxacin;
tri = trimetoprim

TABLE 2

Inhibitory effect of pentane-1,5-diol on various bacteria, including multiple-resistant (MR) bacteria; one inoculate size.

| Bacterial Strain | MIC (% by weight of pentane-1,5-diol) Inoculate Size $10^3$ | MR resistant against fuc | met | van | cip | tri |
|---|---|---|---|---|---|---|
| *Alphastreptococci* 912 × 1135 | 7.5 | | | | | |
| *Alphastreptococci* 912 × 1137 | 5.0 | | | | | |
| *Alphastreptococci* 912 × 1138 | 5.0 | | | | | |
| *Alphastreptococci* 912 × 1139 | 7.5 | | | | | |
| *Alphastreptococci* 912 × 1200 | 7.5 | | | | | |
| *S. pyogenes*, group A 912 × 1115 | 7.5 | | | | | |
| *S. pyogenes*, group A 912 × 1119 | 7.5 | | | | | |
| *S. pyogenes*, group A 912 × 1121 | 7.5 | | | | | |
| *S. pyogenes*, group A 912 × 1090 | 7.5 | | | | | |
| *S. pyogenes*, group A 912 × 1131 | 7.5 | | | | | |
| *Streptococcus* group G 915 × 1095 | 7.5 | | | | | |
| *Streptococcus* group G 915 × 1146 | 7.5 | | | | | |
| *Streptococcus* group G 900 × 1714 | 10.0 | | | | | |
| *Streptococcus* group G 916 × 10985 | 7.5 | | | | | |
| *Strepotocccus* group G 912 × 1106 | 7.5 | | | | | |
| *Streptococcus* group C 912 × 1185 | 10.0 | | | | | |
| *Streptococcus* group C 912 × 1114 | 10.0 | | | | | |
| *Streptococcus* group C 900 × 1618 | 7.5 | | | | | |
| *Acinetobacter* 921 × 16968 | 5.0 | | | | | |
| *Acinetobacter* 921 × 113359 | 2.5 | | | | | |
| *Acinetobacter* 516 × 748 | 2.5 | | | | | |
| *Acinetobacter* 514 × 1224 | 5.0 | | | | | |
| *Acinetobacter* 116 × 305 | 5.0 | | | | | |
| *Acinetobacter* 117 × 217 | 5.0 | | | | | |
| *S. maltophilia* 921 × 16157 | 5.0 | | | | | |
| *S. maltophilia* 515 × 1269 | 2.5 | | | | | |
| *S. maltophilia* 516 × 679 | 5.0 | | | | | |
| *S. maltophilia* 515 × 695 | 5.0 | | | | | |
| *S. maltophilia* 900 × 1230 | 5.0 | | | | | |
| *P. aeruginosa* 921 × 17701 | 5.0 | | | | + | + |
| *P. aeruginosa* 921 × 17748 | 5.0 | | | | − | + |
| *P. aeruginosa* 921 × 17756 | 5.0 | | | | + | + |

Example 2

Acute toxicity of pentane-1,5-diol. The acute toxicity of pentane-1,5-diol was tested for peroral and topical administration as well as on inhalation.

Peroral administration. Varying doses of pentane-1,5-diol were administered to male Carworth-Wistar rats weighting from 90 to 120 g). The dose was logarithmically increased by a factor of 2. Over a fortnight period $LD_{50}$ was found to be 5.89 g/kg body weight. For test conditions, see: H F Smyth et al., Range finding toxicity data: List VI. Ind. Hygiene J. 1962: March-April; 59-97.

Topical administration. The penetration of rabbit skin was tested with a cuff model. The hair on the back of four male rabbits weighing from 2.5 to 3.5 kg was removed by shaving, the diol applied to the skin with a pipette, and the skin sealed with polyethylene film for 24 hrs. During the test period the animals were immobilised. After the exposure the animals were observed over a fortnight period. Even at the highest tested dose, 20 ml/kg, the animals survived.

Inhalation. Six rats were made to breath air saturated with pentane-1,5-diol for 8 hrs. None of the animals died.

Example 3

Skin irritation test with a medical patch provided with a pentane-1,5-diol composition. A sterile medical cotton patch 5×5×1 cm (uncompressed) in size backed by a perforated polyethylene film was provided with about 3 g of pentane-1,5-diol on its front side and positioned against the skin of a male volunteer (upper left arm) for a period of 24 hrs. Upon removal of the patch the skin seemed free from irritation.

The invention claimed is:

1. A method of inhibiting the growth of multiple-resistant bacteria comprising topical administration of a pharmaceutical composition comprising 15% by weight or more of pentane-1,5-diol as multiple-resistant bacteria bacteriostatic agent and a pharmaceutical acceptable carrier,
   wherein said composition is essentially free of a bacteriostatic agent other than pentane-1,5-diol, and
   wherein the multiple-resistant bacteria is at least one member of the group consisting of *Staphylococcus aureus* resistant to methicillin or fucidic acid, coagulation-negative staphylococci resistant to fucidic acid, *Enterococcus* resistant to fucidic acid, vancomycin, ciprofloxacin or trimetoprim, *Acinetobacter* resistant to cefadroxil, nitrofurantin or mecillinam, *Pseudomonas aeruginosa* resistant to vancomycin, ciprofloxacin or trimetoprim, and trimetoprin resistant *E. coli*.

2. The method of claim 1, wherein the carrier comprises a patch of a woven or non-woven material or a combination thereof.

3. The method of claim 1, wherein the composition is applied to a surface contaminated by said bacteria.

4. The method of claim 3, wherein the carrier is an aqueous carrier.

5. The method of claim 4, wherein the aqueous carrier comprises a thickening agent.

6. The method of claim 5, wherein said thickening agent is a cellulose derivative.

7. The method of claim 3, wherein the carrier comprises a detergent.

8. The method of claim 1, wherein the carrier comprises a patch of a woven or non-woven material or a combination thereof.

9. A method of disinfecting a non-porous surface contaminated with multiple resistant bacteria, comprising:
   providing a disinfecting composition comprising 15% or more by weight of pentane-1,5-diol as multiple-resistant bacteria bacteriostatic agent and a carrier therefor;
   applying said composition to said surface;
   optionally, keeping said composition in contact with said surface for a period of time from 5 min to 24 hrs at ambient temperature, and
   rinsing said surface with water or an aqueous detergent composition,
wherein said composition is essentially free of a bacteriostatic agent other than pentane-1,5-diol, and
wherein the multiple-resistant bacteria is at least one member of the group consisting of *Staphylococcus aureus* resistant to methicillin or fucidic acid, coagulation-negative staphylococci resistant to fucidic acid, *Enterococcus* resistant to fucidic acid, vancomycin, ciprofloxacin or trimetoprim, *Acinetobacter* resistant to cefadroxil, nitrofurantin or mecillinam, *Pseudomonas aeruginosa* resistant to vancomycin, ciprofloxacin or trimetoprim, and trimetoprin resistant *E. coli*.

10. The method of claim 3, wherein the carrier comprises a patch of a woven or non-woven material or a combination thereof.

11. The method of claim 1, wherein the carrier is an aqueous carrier.

12. The method of claim 11, wherein the aqueous carrier comprises a thickening agent, a detergent or both.

13. The method of claim 6, wherein said thickening agent is selected from the group consisting of methyl cellulose, hydroxymethyl cellulose, and hydroxymethyl-propyl cellulose.

14. The method of claim 7, wherein the detergent is a salt of a fatty acid.

15. The method of claim 8, wherein the patch is a cotton patch.

16. The method of claim 1, wherein multiple-resistant bacteria is at least one member of the group consisting methicillin-resistant *Staphylococcus aureus*, and vancomycin-resistant enterococci.

* * * * *